United States Patent
Griswold et al.

(10) Patent No.: US 8,412,352 B2
(45) Date of Patent: Apr. 2, 2013

(54) COMMUNICATION DIPOLE FOR IMPLANTABLE MEDICAL DEVICE

(75) Inventors: Erik C. Griswold, Penngrove, CA (US); James Calvin Allan, Santa Rosa, CA (US)

(73) Assignee: Medtronic, Inc., Minneapolis, MN (US)

(*) Notice: Subject to any disclaimer, the term of this patent is extended or adjusted under 35 U.S.C. 154(b) by 223 days.

(21) Appl. No.: 13/047,846

(22) Filed: Mar. 15, 2011

(65) Prior Publication Data
US 2012/0197349 A1  Aug. 2, 2012

Related U.S. Application Data

(60) Provisional application No. 61/437,198, filed on Jan. 28, 2011.

(51) Int. Cl.
*A61N 1/05* (2006.01)
(52) U.S. Cl. .................................................. 607/126
(58) Field of Classification Search ........... 607/126–132
See application file for complete search history.

(56) References Cited

U.S. PATENT DOCUMENTS

| | | | |
|---|---|---|---|
| 4,987,897 A | 1/1991 | Funke | |
| 5,480,416 A | 1/1996 | Garcia et al. | |
| 5,925,069 A | 7/1999 | Graves et al. | |
| 7,047,076 B1 | 5/2006 | Li et al. | |
| 7,452,334 B2 | 11/2008 | Gianchandani et al. | |
| 7,512,448 B2 | 3/2009 | Malick et al. | |
| 7,747,302 B2 | 6/2010 | Milledge et al. | |
| 7,876,282 B2 | 1/2011 | Keilman et al. | |
| 2005/0277839 A1 | 12/2005 | Alderum et al. | |
| 2006/0161225 A1 | 7/2006 | Sormann et al. | |
| 2006/0259088 A1 | 11/2006 | Pastore et al. | |
| 2007/0260294 A1 | 11/2007 | Schulman et al. | |
| 2010/0179449 A1 | 7/2010 | Chow et al. | |

FOREIGN PATENT DOCUMENTS

| | | |
|---|---|---|
| EP | 0362611 A1 | 4/1990 |
| WO | 00/13585 | 3/2000 |
| WO | 2004068748 A1 | 8/2004 |
| WO | 2006124729 A2 | 11/2006 |
| WO | 2007/028035 A2 | 3/2007 |
| WO | 2007047681 A2 | 4/2007 |

OTHER PUBLICATIONS (PCT/US2012/020133) PCT Notification of Transmittal of the International Search Report and the Written Opinion of the International Searching Authority, 14 pages.
Wegmuller, Marc Simon; "Intra-Body Communication for Biomedical Sensor Networks"; Dissertation submitted to Eth Zurich; 2007; Diss. ETHD No. 17323; 161 pages.
(PCT/US2012/022889) PCT Notification of Transmittal of the International Search Report and the Written Opinion of the International Searching Authority, 12 pages.

*Primary Examiner* — Brian T Gedeon
(74) *Attorney, Agent, or Firm* — Stephen W. Bauer; Michael J. Ostrom

(57) ABSTRACT

This disclosure is directed to an implantable medical device having a housing that encloses at least a communication module. The implantable medical device also includes a first electrode electrically coupled to the communication module and an electrically conductive fixation mechanism that is mechanically coupled to the housing and electrically coupled to the communication module within the housing. The electrically conductive fixation mechanism includes a dielectric material that covers part of a surface of the fixation mechanism. A portion of the electrically conductive fixation mechanism is not covered by the dielectric material such that the portion of the electrically conductive fixation mechanism is exposed to form a second electrode that is electrically coupled to the communication module. The communication module is configured to communicate using the first electrode and second electrode.

21 Claims, 13 Drawing Sheets

COMMUNICATION DIPOLE FOR IMPLANTABLE MEDICAL DEVICE

This application claims the benefit of U.S. Provisional Application Ser. No. 61/437,198, filed on Jan. 28, 2011, the content of which is incorporated herein by reference in its entirety.

TECHNICAL FIELD

The disclosure relates generally to implantable medical devices and, in particular, to a communication dipole for implantable medical devices.

BACKGROUND

A wide variety of implantable medical devices (IMDs) that sense one or more parameters of a patient, deliver a therapy to the patient, or both have been clinically implanted or proposed for clinical implantation in patients. An IMD may deliver therapy to or monitor a physiological or biological condition with respect to a variety of organs, nerves, muscles, tissues or vasculatures of the patient, such as the heart, brain, stomach, spinal cord, pelvic floor, or the like. The therapy provided by the IMD may include electrical stimulation therapy, drug delivery therapy or the like.

The IMD may exchange communications with another device. The IMD may exchange communications with another device that is implanted, attached to (e.g., worn by) the patient or otherwise located near the patient. The information exchanged may be information related to a condition of the patient, such as physiological signals measured by one or more sensors, or information related to a therapy delivered to the patient. The IMD may also receive information from the other device, such as information that may be used to control or configure a therapy to be provided to the patient. The IMD and the other device may exchange information using any of a variety of communication techniques, including inductive telemetry, magnetic telemetry, radio frequency (RF) telemetry or the like.

SUMMARY

Intra-body communication is one communication scheme that may be used to communicate information to and from an implantable medical device. Intra-body communication uses the body of the patient as the communication channel. The human body has dielectric properties that allow the body to act as a transmission medium for electrical currents. Thus, intra-body wireless communication exploits the transmission channel of electrolytic-galvanic coupling with the device electrodes and the ion medium (or other properties) of cellular fluids of the patient. A transmit dipole of either an IMD or an external device applies a modulated electrical current between a pair of electrodes forming a transmit dipole of the transmitting device. A pair of electrodes of the receiving device, which are also in contact with the body of the patient, form a receive dipole that receives the modulated signal as an electric potential difference across the pair of electrodes forming the receive dipole.

Due to the small size of IMDs, and especially devices configured for implantation within the vasculature of the patient, the distance between electrodes forming the communication dipole is typically limited. Electrodes used for intra-body communication may, for example, typically be placed at opposite ends of a housing of the IMD. It is desirable, however, to increase the distance between the electrodes of the communication dipole to increase the strength of the communication signal transmitted via intra-body communication. In accordance with the techniques of this disclosure, the IMD is configured to utilize a portion of a fixation mechanism of the IMD as one or both of the electrodes of the communication dipole, thereby increasing the distance separating the electrodes. In instances in which the fixation mechanism is utilized for only one of the dipole electrodes, the other dipole electrode may be formed on or integrated in the housing of the IMD.

In one example, the disclosure is directed to an implantable medical device comprising a housing that encloses at least a communication module, a first electrode electrically coupled to the communication module and an electrically conductive fixation mechanism that is mechanically coupled to the housing and electrically coupled to the communication module within the housing. The electrically conductive fixation mechanism includes a dielectric material that covers part of a surface of the fixation mechanism. A portion of the electrically conductive fixation mechanism is not covered by the dielectric material such that the portion of the electrically conductive fixation mechanism is exposed to form a second electrode that is electrically coupled to the communication module. The communication module is configured to communicate using the first electrode and second electrode.

In another example, the disclosure is directed to an apparatus comprising a housing that includes a communication module and a sensor to sense at least one parameter of a patient. The apparatus also includes a first electrode electrically coupled to the communication module and means for affixing the apparatus to a target location within a patient. The means for affixing is mechanically coupled to the housing and electrically coupled to the communication module within the housing. The means for affixing is formed of a conductive material partially covered by a dielectric material such that a portion of the conductive material is not covered by the dielectric material to form a second electrode that is electrically coupled to the communication module. The communication module is configured to communicate using intra-body communication via the first electrode and second electrode.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
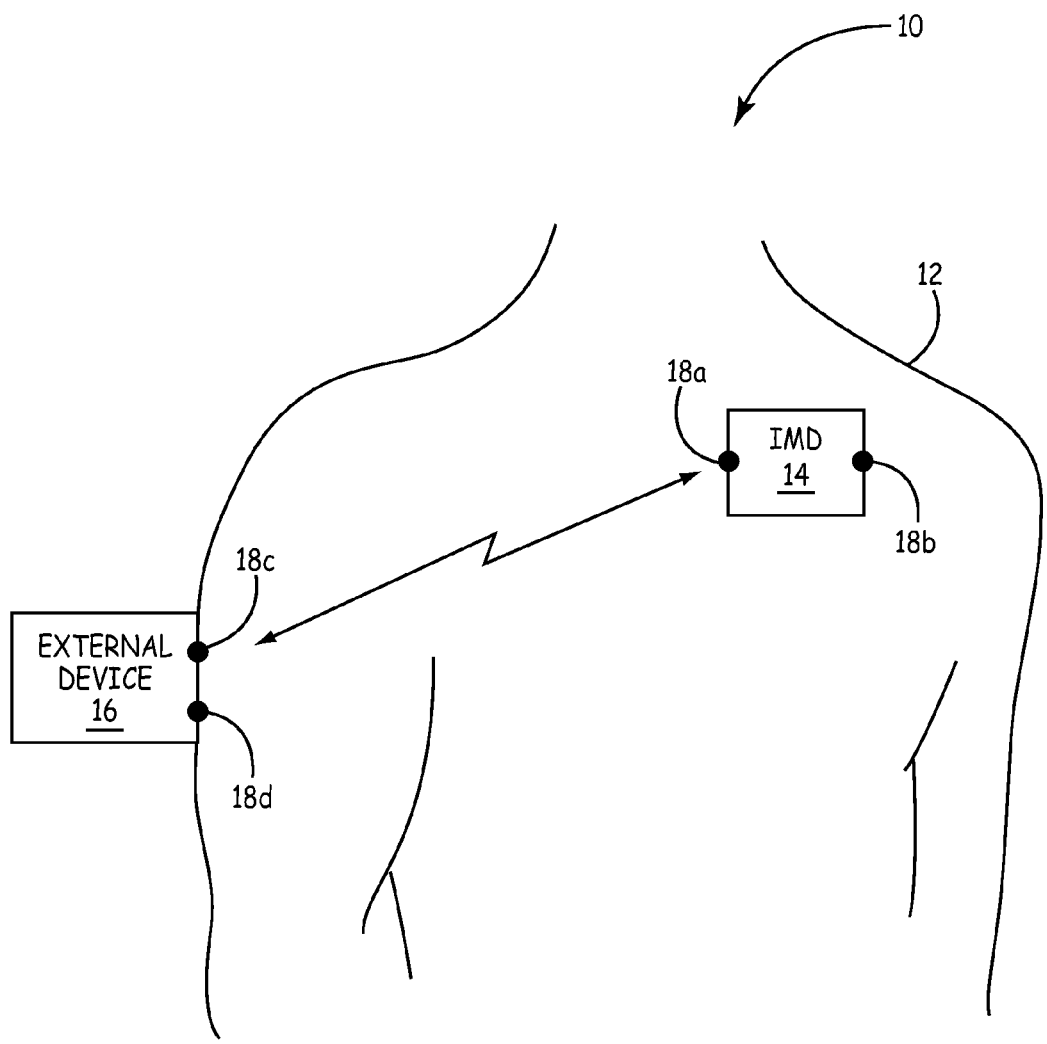
FIG. 1 is a conceptual diagram illustrating an example medical system.

FIG. 1 is a conceptual diagram illustrating an example medical system 10. Medical system 10 includes an implantable medical device (IMD) 14 and an external device 16. Medical system 10 may, however, include more of fewer implanted or external devices.

IMD 14 may be any of a variety of medical devices that sense one or more parameters of patient 12, provide therapy to patient 12 or a combination thereof. In one example, IMD 14 may be a leadless IMD. In other words, IMD 14 is implanted at a targeted site with no leads extending from IMD 14, thus avoiding limitations associated with lead-based devices. Instead, sensing and/or therapy delivery components are integrated with IMD 14. In the case of a leadless sensor, IMD 14 includes one or more sensors that measure the physiological parameter(s) of patient 12. In one example, IMD 14 may comprise an implantable device incorporating a pressure sensor that is placed within a vasculature or chamber of a heart of patient 12.

IMD 14 may, in some instances, provide therapy to patient 12. IMD 14 may provide the therapy to patient 12 as a function of sensed parameters measured by the sensor of IMD 14 or sensed parameters received from another device, such as another IMD or a body worn device. As one example, IMD 14 may be a leadless cardiac IMD that provides electrical stimulation therapy (e.g., pacing, cardioversion, defibrillation, and/or cardiac resynchronization therapy) to the heart of patient 12 via one or more electrodes as a function of sensed parameters associated with the heart. In yet a further example, IMD 14 may provide therapy to patient 12 that is not provided as a function of the sensed parameters, such as in the context of neurostimulation. Although described above in the context of electrical stimulation therapy, IMD 14 may provide other therapies to patient 12, such as delivery of a drug or other therapeutic agent to patient 12 to reduce or eliminate the condition of the patient and/or one or more symptoms of the condition of the patient, or provide no therapy at all.

External device 16 communicates with IMD 14 using intra-body communication. Intra-body communication as used herein refers to a data transmission scheme that uses the human body as the communication channel. The human body has dielectric properties that allow the body to act as a transmission medium for electrical currents. In particular, the intra-body wireless communication scheme exploits the transmission channel of electrolytic-galvanic coupling with the device electrodes and the ion medium (or other properties) of cellular fluids of patient 12. External device 16 and IMD 14 may communicate using intra-body communication over frequencies ranging from a few kilohertz to a few megahertz. Higher frequency communication signals may be used to increase data transmission rates.

IMD 14 and external device 16 each include respective electrodes 18a-d used for intra-body communication. Electrodes 18a and 18b of IMD 14 can form both a receive dipole and a transmit dipole of IMD 14, and electrodes 18c and 18d of external device 16 can form both a receive dipole and a transmit dipole of external device 16, each for use in intra-body communication. A transmit dipole of either IMD 14 or external device 16 injects modulated electrical current between the pair of electrodes forming the transmit dipole, which introduces a modulated current into the body of patient 12. A receive dipole of the other one of IMD 14 or external device 16, also in contact with the body of patient 12, receives the modulated signal as an electric potential difference across the pair of electrodes which are also in contact with the body of patient 12. Electrodes 18a and 18b of IMD 14 and the electrodes 18c and 18d of external device 16 can each be configured to function as either the transmit dipole or the receive dipole.

External device 16 may communicate with IMD 14 via intra-body communication to retrieve information from IMD 14, such as the parameters measured by the one or more sensors of IMD 14 or information related to therapies delivered to patient 12. For example, information relating to monitored physiological parameters of patient 12 can be stored in a memory of IMD 14 and periodically transmitted to external device 16. Information can also be transmitted in the opposite direction (i.e. from the external device 16 to IMD 14), for example, when external device 16 provides programming information to IMD 14.

External device 16 may process the information from IMD 14 to monitor a condition of patient 12. In the case of an implantable device incorporating a pressure sensor, for example, external device 16 may receive pressure measurements from IMD 14 and process pressure measurements to monitor for a cardiac condition, such as heart failure. As another example, external device 16 may process sensed cardiac signals to monitor for a cardiac condition, such as tachycardia or bradycardia.

External device 16 may present the information to patient 12 via a display or other user interface. External device 16 may also relay the information received from IMD 14 to another IMD using intra-body communication or other type of communication, e.g., inductive, magnetic or radio frequency (RF) communication. Likewise, external device 16 may relay the information received from IMD 14 to an external device via another wireless communication scheme, such as RF communication, Bluetooth or the like. External device 16 may also transmit information to IMD 14, such as information identifying a condition of patient 12, information sensed by a sensor of external device 16 or information sensed by a sensor of another IMD implanted within patient 12. The information transmitted to IMD 14 may, in some instances, control delivery of therapy by IMD 14.

External device 16 may be a body worn device, such as a watch, necklace, armband, belt, ring, bracelet, patch, or other device that is configured to be attached to, worn by, placed on or otherwise coupled to a body of patient 12 in order to contact electrodes 18c and 18d to the skin of patient 12. Alternatively, external device 16 may be a handheld computing device, such as a cellular telephone, smart phone, pager, or personal digital assistant (PDA), that includes electrodes 18c and 18d configured to be placed in contact with the skin of patient 12.

Although FIG. 1 is described in the context of a medical system 10 having an IMD 14 communicating with an external device 16, IMD 14 may also communicate with another implantable medical device using intra-body communication in a similar manner to that described above.

Figure 2:
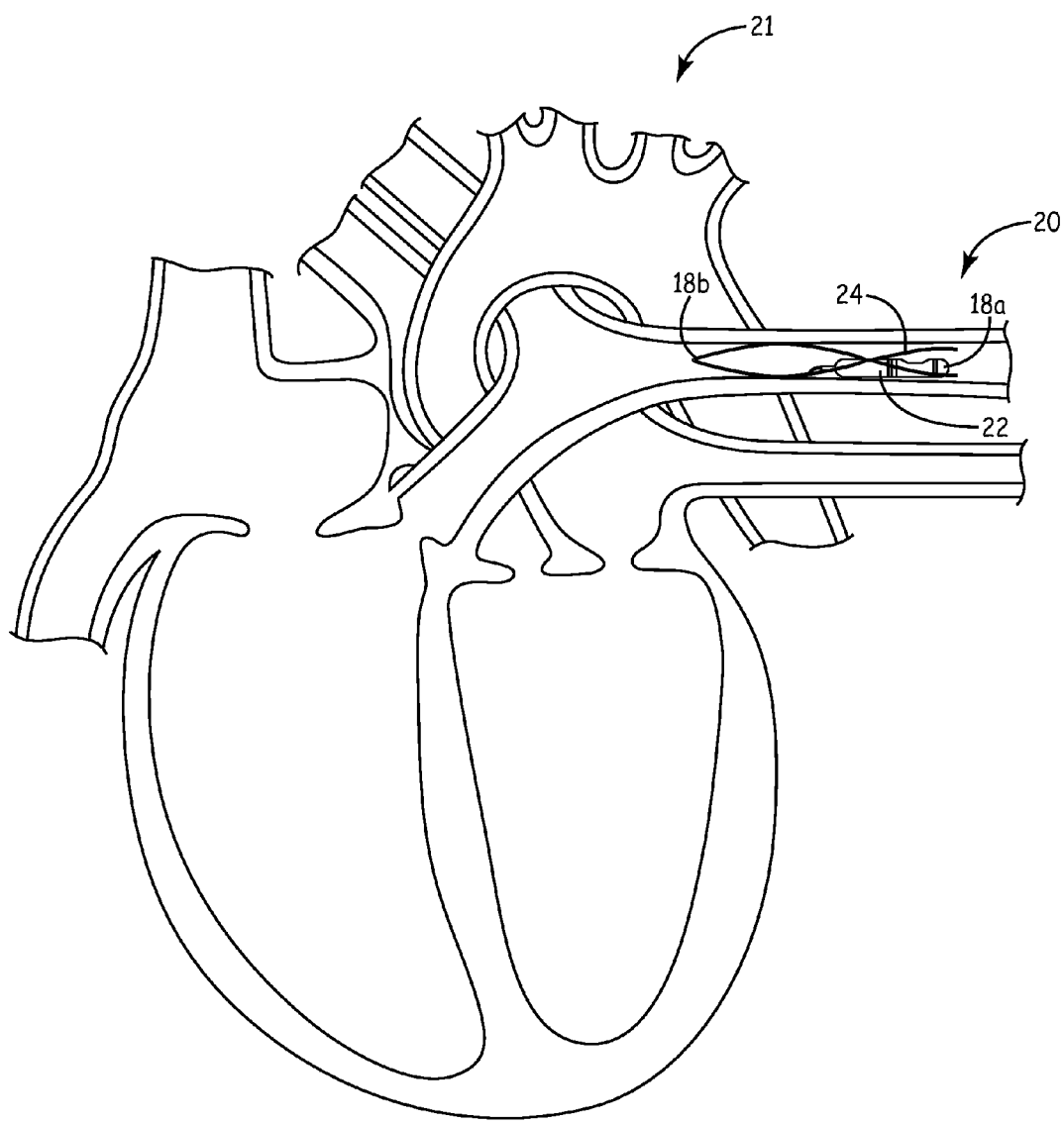
FIG. 2 illustrates an IMD implanted in a heart of a patient.
Figure 3A:
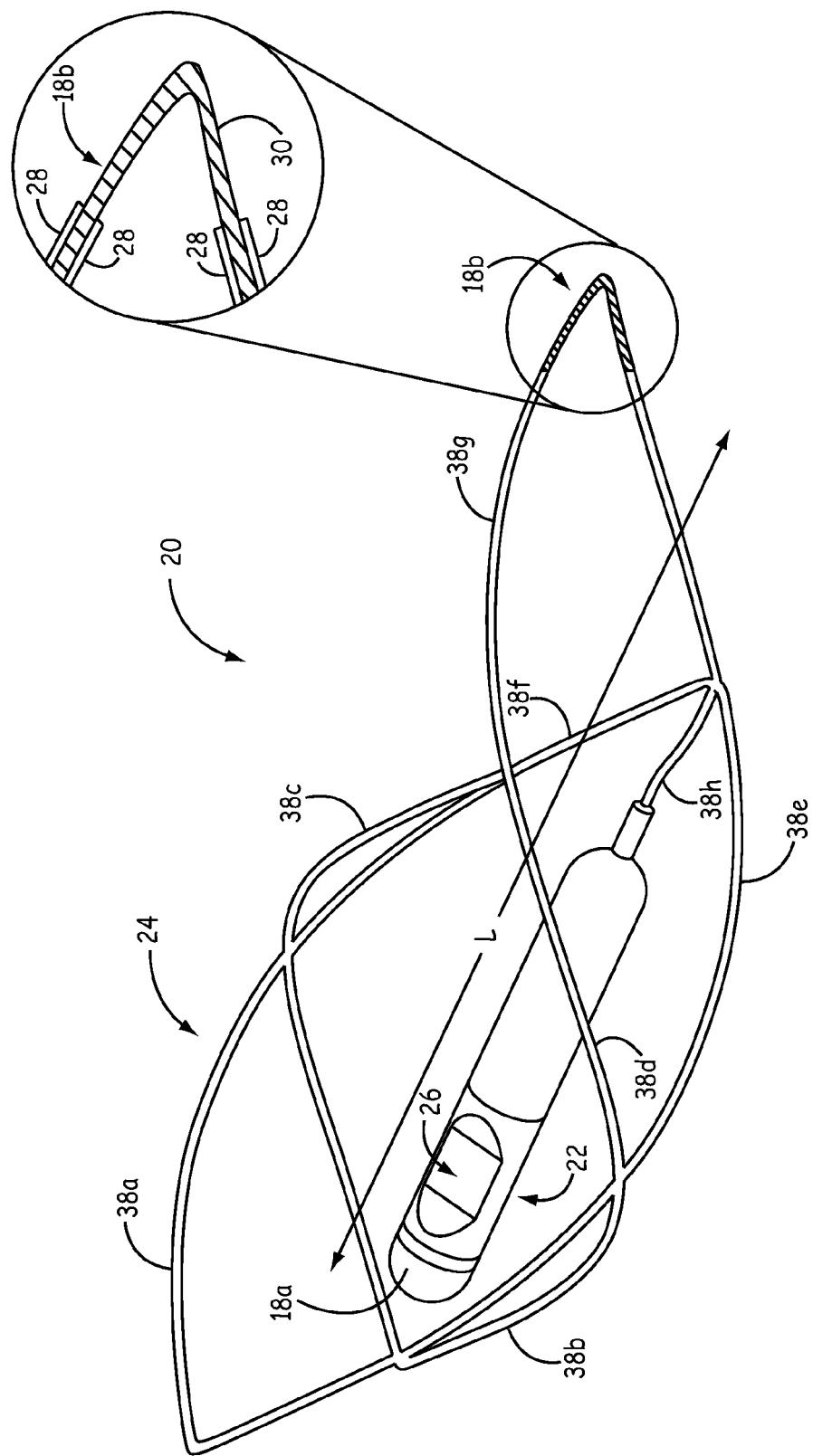
FIGS. 3A-3C illustrate enlarged views of the IMD of FIG. 2 from various viewpoints.
Figure 3B:
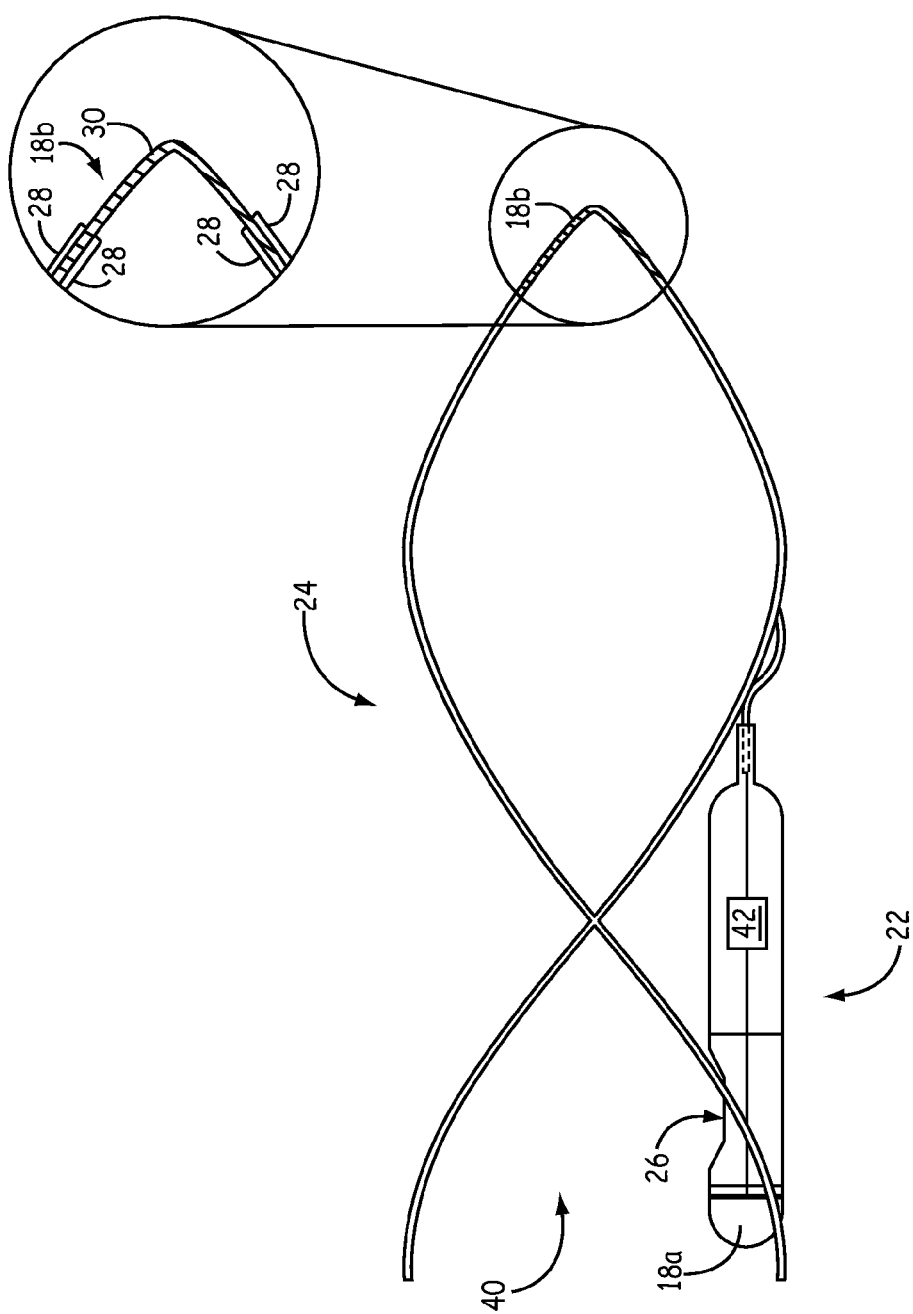
Figure 3C:
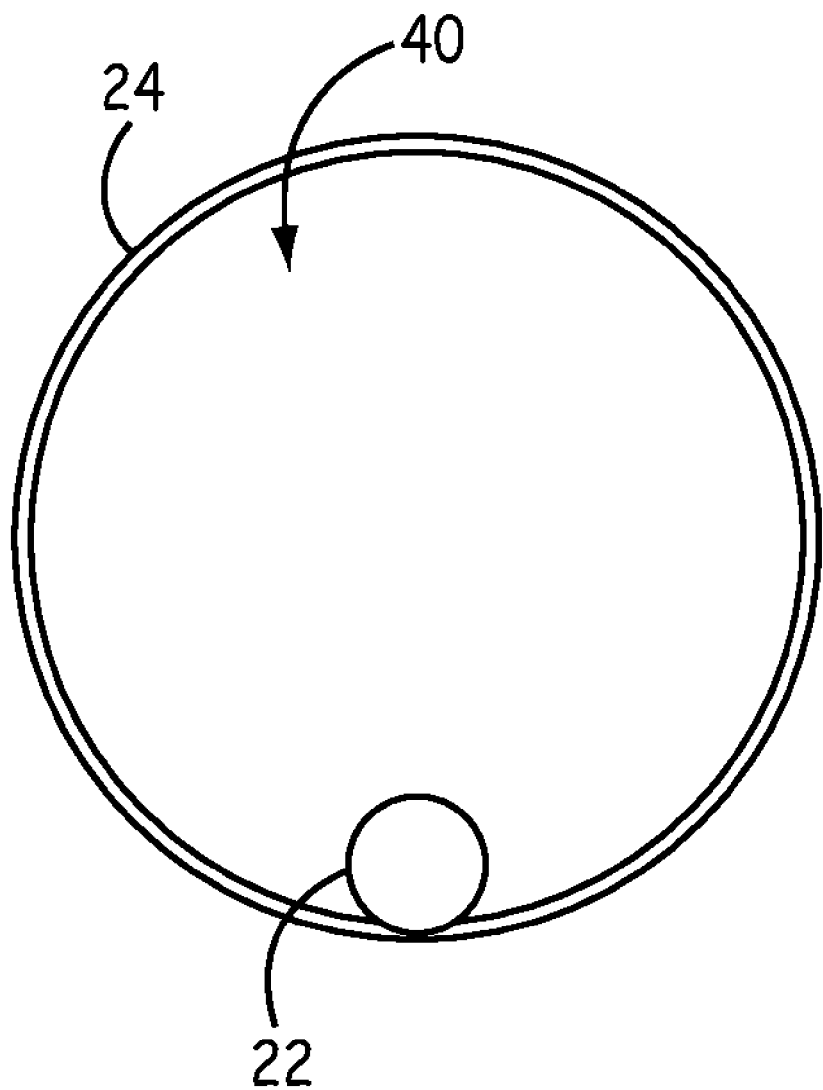

FIGS. 2 and 3A-3C are schematic diagrams illustrating an example IMD 20. IMD 20 may correspond with IMD 14 of FIG. 1. FIG. 2 illustrates IMD 20 implanted in a heart 21 of a patient 12. In the example illustrated in FIG. 2, IMD 20 is implanted in the pulmonary artery (PA) of heart 21. However, IMD 20 may be placed within or near other portions of heart 21, such as in one of the chambers (atrial or ventricular), veins, vessels, arteries or other vasculature of heart 21, such as the aorta, renal arteries, or inferior or superior vena cava. FIGS. 3A-3C illustrate enlarged views of IMD 20 from various viewpoints. In particular, FIG. 3A illustrates an angled view from an aerial perspective, FIG. 3B illustrates a side view and FIG. 3C illustrates an end view.

IMD 20 includes a housing 22 and a fixation mechanism 24. Housing 22 and fixation mechanism 24 of IMD 20 may be sized and shaped to fit within a target location. In the example illustrated in FIGS. 2 and 3A-3C, housing 22 has a long, thin cylindrical shape (e.g., capsule-like shape) to accommodate placement in the pulmonary artery of heart 21. Since IMD 20 may be placed within or near other portions of heart 21 or other locations within the body of patient 12, the size and shape of IMD 20 may vary based on the desired implant location. Additionally, the size and shape of housing 22 may vary depending on the number and type of sensors incorporated within housing 22. For example, housing 22 may be formed in a different shape to accommodate placement within a chamber of heart 21, along a spine, in a brain, or other location within or on patient 12. As such, the techniques described in this disclosure should not be limited by the shape of housing 22 described herein.

Housing 22 hermetically encloses components of IMD 20, such as at least one processor, memory, power source, communication circuitry, sensing circuitry, therapy circuitry or the like. For ease of illustration, FIG. 3B illustrates only a communication module 42 within housing 22. However, other components of IMD 20, such as those described with respect to FIG. 9, may also be enclosed within housing 22.

Housing 22 may be formed of any of a variety of materials including conductive materials or a combination of conductive and non-conductive materials. Examples of biocompatible, conductive materials includes titanium, stainless steel, superalloy (such as a nonmagnetic, nickel-cobalt-chromium-molybdenum alloy), platinum or the like. Examples of biocompatible, non-conductive materials include silicone, parylene, polyurethane, epoxy, acetyl co-polymer plastics, PolyEtherEtherKetone (PEEK), liquid crystal polymer (LCP) plastics, or the like. In one example, housing 22 is formed of a conductive material coated with a non-conductive coating that covers all of housing 22 except the end portion of housing 22 forming electrode 18a. Electrode 18a is electrically isolated from the rest of the conductive housing and is electrically connected to communication module 42 enclosed within housing 22 via an electrical interconnect, including, but not limited to a wire or conductive trace.

Housing 22 also includes a sensor for sensing one or more parameters of patient 12. In the example illustrated in FIGS. 2 and 3A-3C, housing 22 includes a pressure sensor 26 that obtains pressure measurements of an environment surrounding housing 22. Thus, IMD 20 may be an active leadless pressure sensor system designed to continuously monitor blood pressure and transmit the pressure measurements to external device 16 or another implanted device. However, IMD 20 may sense pressure measurements of other locations of heart 21 depending on the location of implantation.

In the example illustrated in FIGS. 2 and 3A-3B, housing 22 is formed to have an opening that exposes pressure sensor 26 to the environment at the target location. The opening of housing 22 is illustrated in FIGS. 2 and 3A-3B as being located along a length of housing 22. However, in other embodiments, the opening of housing 22 may be located on either end of housing 22. In any case, pressure sensor 26 is exposed to the surrounding environment to obtain pressure measurements of the surrounding environment.

Pressure sensor 26 may include a deformable diaphragm that moves in response to changes in the pressure of the environment to which it is exposed. Accordingly, there is a direct relationship between the movement of the diaphragm and the change in pressure. The diaphragm of pressure sensor 26 may be positioned adjacent to the opening of housing 22 so that pressure from the surrounding environment will act upon the diaphragm through the opening of housing 22. It is understood that in accordance with one or more embodiments, the diaphragm may be a component of a capacitor structure used in generating capacitive measurements indicative of the pressure of the surrounding environment. In other words, pressure exerted on the diaphragm causes a corresponding movement of the diaphragm which in turn alters a measured capacitance. As such, the measured capacitance corresponds to the pressure from the surrounding environment acting on the diaphragm. By way of example only and without limitation, pressure sensor 26 may comprise a pressure sensor constructed in a manner similar to that described in commonly assigned U.S. Pat. No. 6,221,024, entitled "Implantable Pressure Sensor and Method of Fabrication," U.S. patent application Ser. No. 12/512,869 filed Jul. 30, 2009 and entitled "Implantable Pressure Sensor with Membrane Bridge," and U.S. Pat. No. 7,591,185, entitled "Pressure Sensor Configurations for Implantable Medical Electrical Leads" the contents of each of which are hereby incorporated by reference for their description of pressure sensors.

Although described above as a capacitive pressure sensor, pressure sensor 26 may be any sort of pressure sensing device, such as an electromagnetic pressure sensor that measures displacement of the diaphragm by means of changes in inductance (reluctance), linear variable differential transformer (LVDT), Hall Effect or eddy currents, a piezoelectric pressure sensor, optical pressure sensor, or any other pressure sensor. Housing 22 may include other types of sensors instead of or in addition to pressure sensor 26, such as pH sensor, oxygen sensor, temperature sensor, electrode, or any other type of sensor.

Fixation mechanism 24 affixes IMD 20 to the target location, such as the wall of the pulmonary artery in the example illustrated in FIG. 2. Fixation mechanism 24 of FIGS. 2 and 3A-3C is a generally tubular or cylindrical stent-like structure that is configured to lodge against a vessel wall when implanted. Fixation mechanism 24 is configured such that housing 22 of IMD 20 is adjacent to the wall of the vasculature when implanted. In other embodiments, fixation mechanism 24 is configured such that housing 22 of IMD 20 is not in contact with the wall of the vasculature when implanted. Instead, housing 22 of IMD 20 may be substantially radially centered within vasculature when implanted or otherwise offset from the wall of the vasculature.

Fixation mechanism 24 includes a plurality of struts 38a-h that are arranged to form fixation mechanism 24. In particular, struts 38a-h are arranged to form the stent-like structure having a lumen 40. The number of struts and arrangement of struts may vary depending upon the desired length and structural rigidity of fixation mechanism 24. For example when the target implant site is relatively short, it would be desirable for fixation mechanism 24 to have a smaller number of struts arranged to form a short fixation mechanism. The material from which struts 38a-38h are made may be capable of being manipulated such that fixation mechanism 24 may be radially compressed or otherwise manipulated to aid in delivery of IMD 20 to the target location. When located at the target location, fixation mechanism may be expanded in situ, e.g., via inflation of a balloon (not shown), such that at least a portion of struts 38 securely engage the vessel wall. Struts 38a-h may, for example, be made from a variety conductive materials suitable for implantation, including, but not limited to, nickel-titanium (nitinol), stainless steel, tantalum, nickel, titanium, nickel-cobalt-chromium-molybdenum "superalloy," combinations of the above, and the like.

In some embodiments, at least a portion of housing 22 of IMD 20 is positioned within lumen 40 defined by fixation mechanism 24. The diameter of lumen 40 is greater than the diameter of housing 22 such that the portion of housing 22 may be positioned within lumen 40 while still allowing blood to flow within the pulmonary artery. In the example illustrated in FIGS. 3A-3C, housing 22 of IMD 20 is completely located within lumen 40 defined by fixation mechanism 24. In other embodiments, only a portion of housing 22 may be located within lumen 40. For example, the portion of housing 22 forming first electrode 18a may be extend beyond lumen 40. Disposing at least a portion of housing 22 within lumen 40 reduces the overall length of IMD 20, which may be particularly advantageous when IMD 20 is implanted at a target site having a relatively short landing zone within the vessel. In further embodiments, however, none of housing 22 of IMD 20 may be positioned within lumen 40 defined by fixation mechanism 24.

Fixation mechanism 24 is mechanically coupled to housing 22 via strut 38h. Strut 38h may be mechanically coupled via crimping, welding or other technique. Fixation mechanism 24 is also electrically coupled to communication module 42 by one or more electrical interconnects within housing 22. In one embodiment, the electrical connection to communication module 42 is made when strut 38h is mechanically coupled to housing 22. As indicated with respect to FIG. 1, IMD 20 transmits and/or receives wireless signals via intra-body communication using electrodes 18a and 18b. To transmit wireless signals via intra-body communication, IMD 20 applies a modulated current signal between electrodes 18a and 18b, which causes a current to propagate into the conductive parts of the body (e.g., ion medium of cellular fluids). The current induced in the body by electrodes 18a and 18b results in a potential difference between electrodes 18c and 18d of external device 16 (FIG. 1) which are in contact with the body of patient 12. To receive wireless signals via intra-body communication, electrodes 18a and 18b of IMD 20 detect a potential difference caused by the introduction of current by external device 16.

As described above, IMD 20 is typically a small size to fit within the vasculature of patient 12. Conventionally, electrodes 18a and 18b used for intra-body communication are placed at opposite ends of housing 22. In this case, the maximum distance between electrodes 18a and 18b is limited to the length of housing 22. It is desirable, however, to increase the distance between electrodes 18a and 18b to increase the strength of the communication signal transmitted via intra-body communication. In accordance with the techniques of this disclosure, IMD 20 is configured to utilize a portion of fixation mechanism 24 as one or both of the electrodes, thereby increasing the distance (L) separating the electrodes (sometimes referred to as the dipole length).

In the example illustrated in FIGS. 2 and 3A-3C, a portion of housing 22 is configured as first electrode 18a and a portion of fixation mechanism 24 is configured as second electrode 18b. As described above, struts 38a-h of fixation mechanism 24 may be formed from an electrically conductive material 30. In accordance with the techniques of this disclosure, a dielectric material 28 may be selectively applied such that only a portion of fixation mechanism 24 is exposed to the surrounding environment. The rest of fixation mechanism 24 is covered by the dielectric material 28. The dielectric material may include silicone, parylene, polyurethane, epoxy, acetyl co-polymer plastics, PolyEtherEtherKetone (PEEK), liquid crystal polymer (LCP) plastics, or the like, or a combination of dielectric materials. The thickness of dielectric material 28 may depend on a number of factors, including the properties of the dielectric material and the current amperage used for communication. In on example, the coating of dielectric material of parylene may have a thickness of between approximately 2-20 microns. Again, however, the thickness of dielectric material 28 may vary and this is just one example.

The exposed portion of fixation mechanism 24 (i.e., the electrically conductive material 30 of fixation mechanism 24 not coated by dielectric material 28) therefore functions as the second electrode 18b for intra-body communication. In this manner, the only portion of the conductive fixation mechanism 24 that is exposed directly to the bodily fluid or tissue of patient 12 is the portion of fixation mechanism 24 that functions as the second electrode 18b. In the example illustrated in FIGS. 3A and 3B, a portion of electrically conductive material 30 of strut 38g is exposed to the surrounding environment while the remainder of the conductive material 30 strut 38g and the other struts 38 are covered by dielectric material 28. The portion of the conductive material 30 of strut 38 that is exposed (i.e., not covered by dielectric material 28) is represented by shading.

By using a portion of fixation mechanism 24 as second electrode 18b, the portion of fixation mechanism 24 forming second electrode 18b is a further distance from the first electrode than any other portion of housing 22, thus increasing the distance between electrodes 18a and 18b and the effective dipole length. In some instances, the portion of fixation mechanism 24 forming second electrode 18b is located at a position along fixation mechanism 24 that is the furthest distance from the portion of housing 22 forming first electrode 18a, thus maximizing the distance between electrodes 18a and 18b and the effective dipole length.

Figure 4:
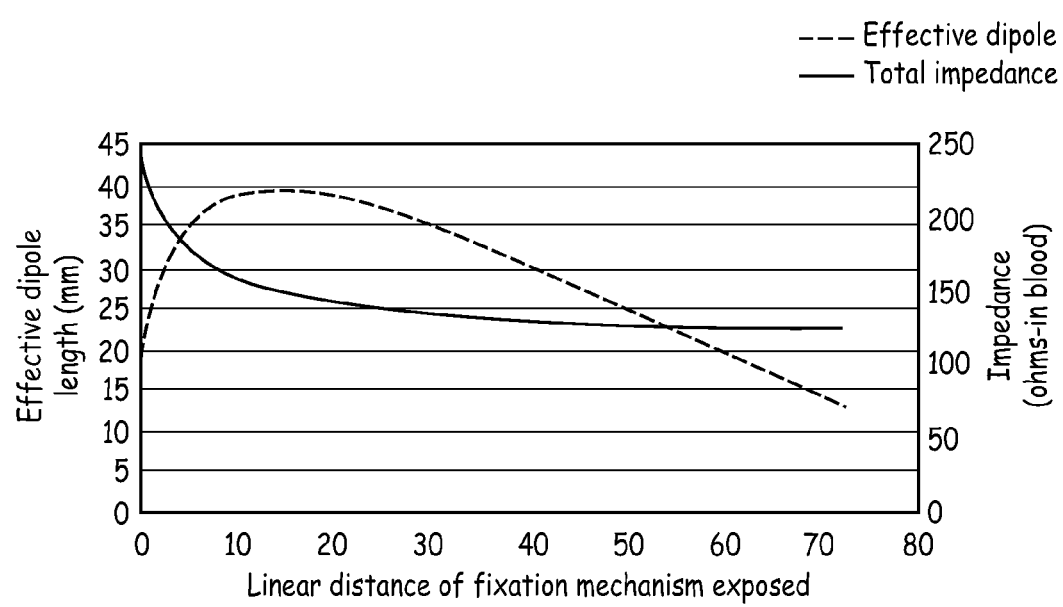
FIG. 4 is a graph illustrating an example plot of effective dipole length and impedance versus the amount of fixation mechanism that is exposed.

In addition to the distance between electrodes 18a and 18b, the amount of conductive material 30 of fixation mechanism 24 that is exposed (i.e., not covered by the dielectric material 28) also affects the effective dipole length. Additionally, the amount of conductive material 30 of fixation mechanism 24 that is exposed further affects the impedance of the dipole. FIG. 4 is a graph illustrating an example plot of effective dipole length and impedance versus the amount of fixation mechanism 24 that is exposed. The x-axis of the graph in FIG. 4 corresponds with percentage of the linear distance of fixation mechanism that is exposed. The y-axis on the left hand side of the graph of FIG. 4 corresponds to effective dipole length (mm) and the y-axis on the right hand side corresponds with impedance in blood (Ohms-in blood).

As illustrated in FIG. 4, the effective dipole length (represented by the dotted line) increases exponentially as the percentage of the linear distance of fixation mechanism 24 that is exposed increases until approximately 20% and then begins to linearly decrease as the percentage of the linear distance of fixation mechanism 24 that is exposed continues to increase. As further illustrated in FIG. 4, the impedance (represented by the solid line) decreases exponentially as the percentage of the linear distance of fixation mechanism 24 that is exposed increases. As such, the amount of fixation mechanism 24 that is exposed may be selected to obtain a balance between effective dipole length and impedance. In one example, the percentage of fixation mechanism 24 that is exposed may be between approximately 5-30% and, more preferably between approximately 10-20%. As will be described with respect to FIGS. 8a-8c, more than one electrode formed by a portion of fixation mechanism 24 may be turned on to increase the linear distance of fixation mechanism 24 and thereby affect the impedance.

Although this disclosure is described with respect to IMD 20 being an implantable pressure sensor implanted within a heart of patient 12, IMD 20 be placed in locations within patient 12, such as within or proximate to a spinal cord, brain, stomach, or pelvic floor, and may sense, sample, and process any of a variety of parameters such as heart activity, muscle activity, brain electrical activity, intravascular pressure, blood pressure, blood flow, acceleration, displacement, motion, respiration, or blood/tissue chemistry, such as oxygen saturation, carbon dioxide, pH, protein levels, enzyme levels or other parameter or combination of parameters. IMD 20 transmits the sensed parameters to another device, such as external device 16 (FIG. 1) or another IMD (not shown), which may in turn monitor a condition of patient 12 or provide therapy to patient 12 as a function of the sensed parameters.

Although illustrated as a stent-like fixation mechanism in FIGS. 2 and 3A-3B, fixation mechanism 24 may be a different fixation mechanism that exerts enough force against, embeds within, extends through or otherwise affixes IMD 20 to the target location. Other fixation mechanisms may include one or more tines, loops, or other mechanism that may be used to affix IMD 20 to the target location, some of which are illustrated and described in FIGS. 5-8.

Figure 5:
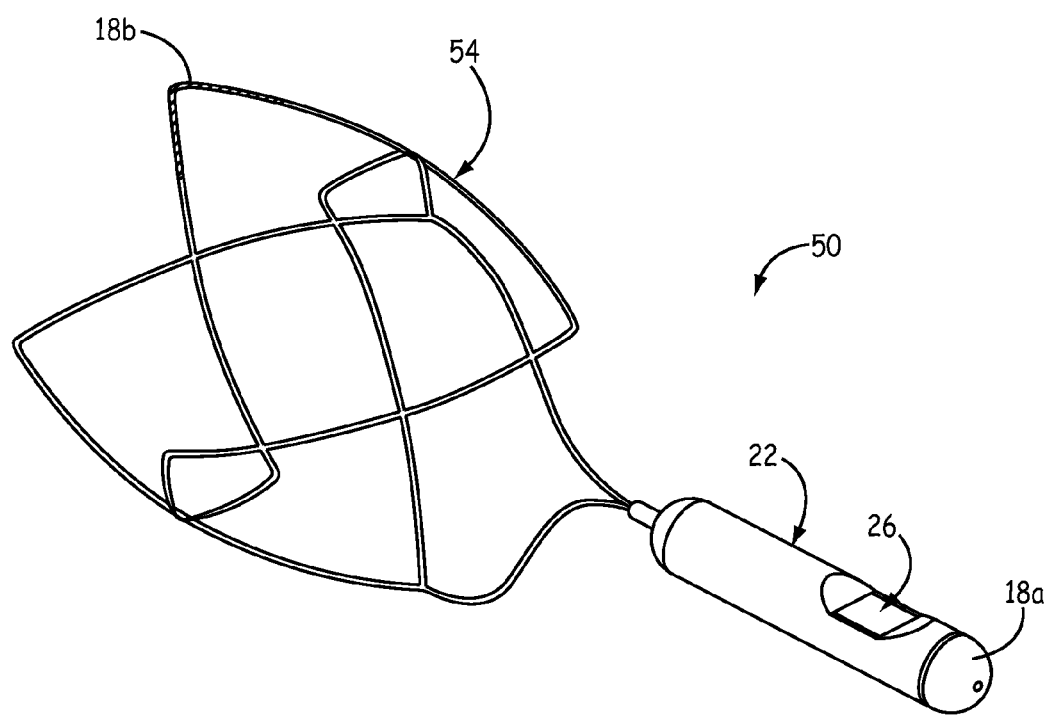
FIG. 5 is a schematic diagram illustrating another example IMD.

FIG. 5 is a schematic diagram illustrating another example IMD 50. IMD 50 is similar to IMD 20 of FIGS. 3A-3C, but includes a different fixation element 54. Fixation element 54 is another stent-like fixation element composed of a number of conductive struts. In the example illustrated in FIG. 5, housing 22 of IMD 50 is not positioned within the lumen defined by fixation mechanism 54.

Like fixation mechanism 24, a portion of fixation mechanism 54 is configured as second electrode 18b. In particular fixation mechanism 54 includes a dielectric material that is selectively applied such that only a portion of fixation mechanism 54 is exposed to the surrounding environment to function as the second electrode 18b for intra-body communication. The rest of fixation mechanism 54 is covered by the dielectric material. The portion of fixation mechanism 54 that is exposed is represented by the shaded portion of fixation mechanism.

Figure 6:
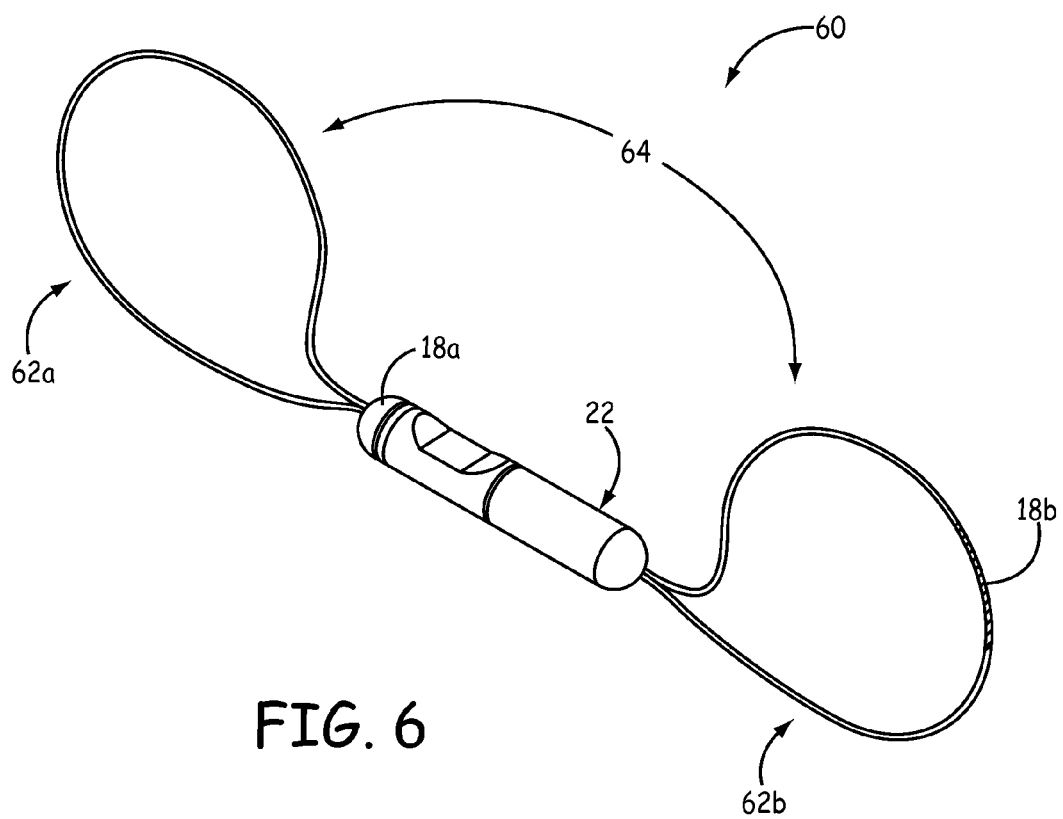
FIG. 6 is a schematic diagram illustrating another example IMD.

FIG. 6 is a schematic diagram illustrating another example IMD 60. IMD 60 includes a housing 22 that is described above with respect to IMD 20 of FIGS. 3A-3C. However, IMD 60 includes a different fixation mechanism 64. Fixation mechanism 64 is a loop fixation mechanism that includes a first loop 62a and a second loop 62b. First loop 62a extends from a first end of housing 22 and loop 62b extends from a second, opposite end of housing 22. Loops 62a and 62b affix IMD 60 within the vasculature due to force applied to the vessel wall by the respective loops 62a and 62b pushing radially against the vessel. Although illustrated in FIG. 6 as including two loops 62a and 62b, fixation mechanism 64 of IMD 60 may include only a single fixation loop (e.g., only loop 62a) or more than two fixation loops.

Loops 62a and 62b may be formed of a conductive material, such as a conductive wire, at least partially covered by a dielectric material. A portion of loop 62b is illustrated as not being covered by the dielectric material such that the exposed portion of loop 62b (represented by the shaded portion of loop 62b) functions as second electrode 18b for intra-body communication in conjunction with electrode 18a that is formed at the end of housing 22. The rest of loop 62b and the entirety loop 62a are covered by the dielectric material.

Figure 7:
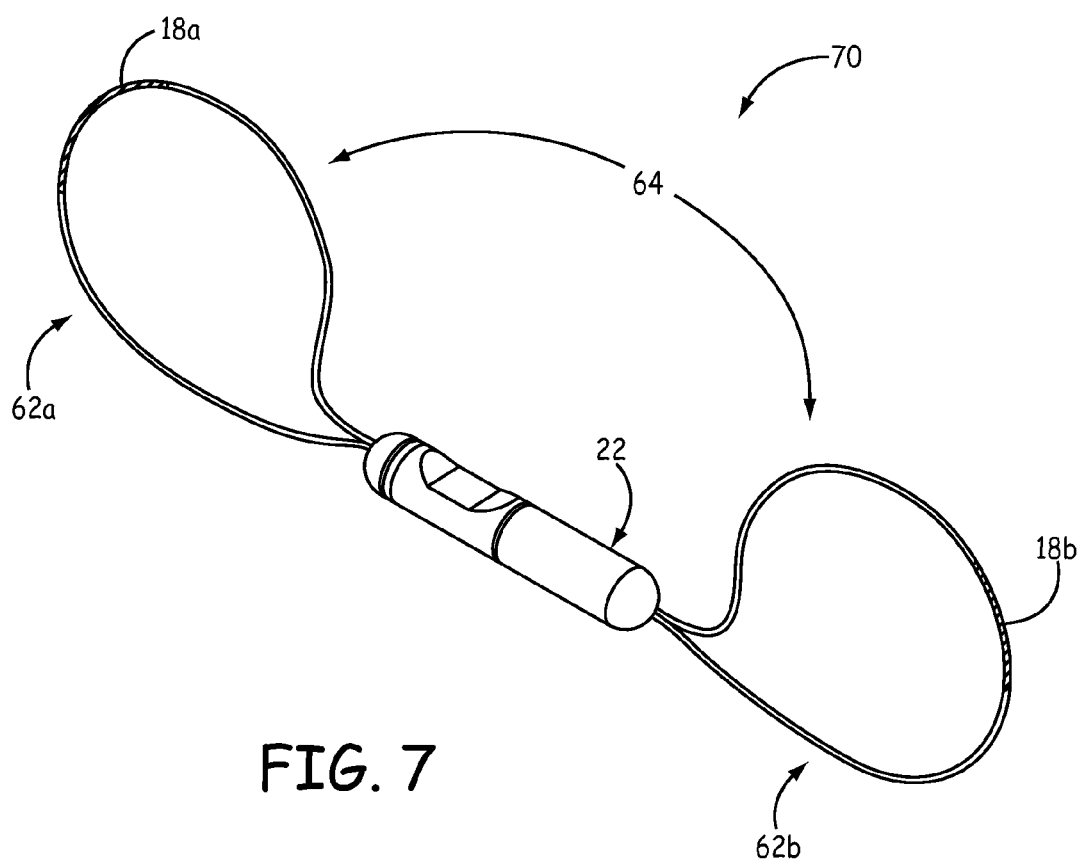
FIG. 7 is a schematic diagram illustrating another example IMD.

FIG. 7 is a schematic diagram illustrating another example IMD 70. IMD 70 conforms substantially to IMD 60 of FIG. 6, but first electrode 18a is formed by a portion of loop 62a instead of by an end of housing 22. In this case, a portion of loop 62a is not covered by the dielectric material such that the exposed portion of loop 62a (represented as the shaded portion of loop 62a) functions as first electrode 18a for intra-body communication. The rest of loop 62a is covered by the dielectric material. Loop 62a is electrically connected to the communication module of IMD 70 to transmit and receive signals in conjunction with electrode 18b formed by loop 62b. Utilizing portions of fixation mechanism 64 as both electrodes 18a and 18b may result in an even larger distance between electrodes 18a and 18b, thereby further extending the effective dipole length.

Figure 8A:
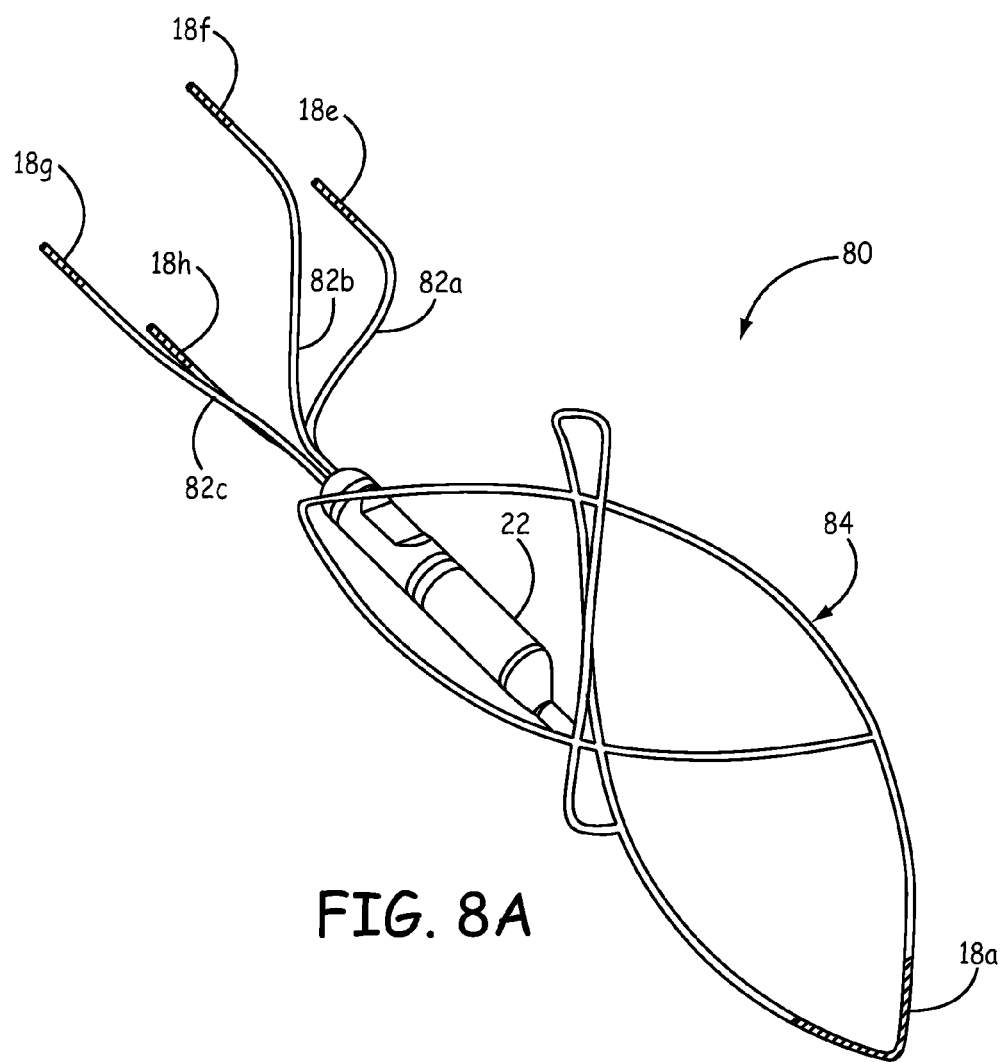
FIGS. 8A-8C illustrate a further example of an IMD.
Figure 8B:
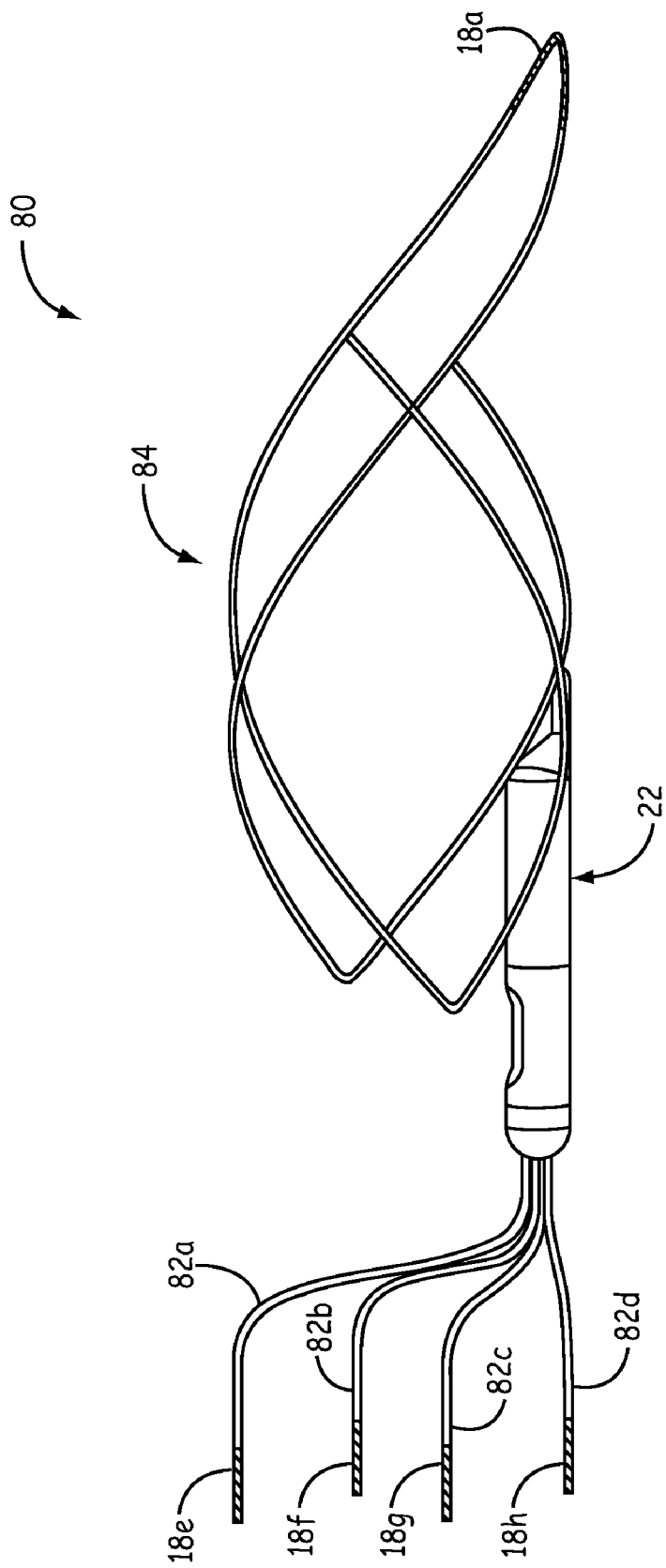
Figure 8C:
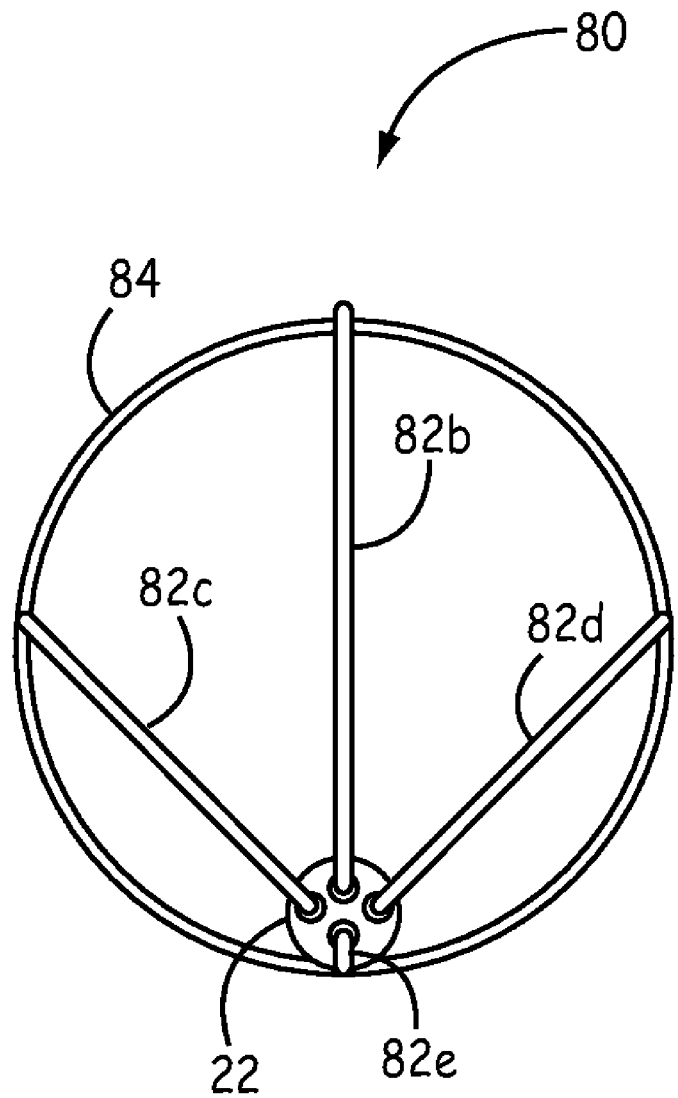

FIGS. 8A-8C illustrate a further example of an IMD 80. IMD 80 includes a housing 22 substantially similar to the housing described in detail above with respect to FIGS. 3A-3C. IMD 80 also includes a fixation mechanism 84 that is similar to fixation mechanism 24 of IMD 20 illustrated in FIGS. 3A-3C. Housing 22 of IMD 80 is positioned partially within the lumen defined by fixation mechanism 84 instead of being completely located within the lumen as illustrated in FIGS. 3A-3C.

In the example illustrated in FIGS. 8A-8C, the end of housing 22 does not function as an electrode used for intra-body communication. Instead, a plurality of struts 82a-d extend from the end of housing 22. Struts 82a-d are formed of a conductive material that is partially covered by a dielectric material such that only a portion of struts 82a-d are exposed to the surrounding environment to function as electrodes for use in intra-body communication. In the example illustrated in FIGS. 8A-8C, a distal end of each of struts 82a-d is exposed to the surrounding environment to form electrodes 18e-h, respectively. Struts 82a-d may or may not additionally function as part of the fixation mechanism for fixating IMD 80 to the target location.

As shown in the end view illustrated in FIG. 8C, each of struts 82a-d is attached to housing 22 by a separate feed through. In this manner, each of the electrodes 18e-h associated with respective struts 82a-d is electrically isolated from one another. Struts 82a-d are electrically coupled to the communication module of IMD 80 such that any of electrodes 18e-h may be used for intra-body communication in conjunction with electrode 18a formed by an exposed portion of fixation mechanism 24 or one another. Struts 82a-d may be electrically coupled to the communication module (not shown) via a switching device (not shown) that may selectively couple one of the electrodes 18e-h to the communication module of IMD 80. In this manner, IMD 80 has the ability to switch electrode configurations used for intra-body communication, thereby providing transmit dipole and receive dipole diversity.

The signal received by external device 16 at electrodes 18c and 18d (FIG. 1), which corresponds to the electric potential difference between electrodes 18c and 18d, is a function of the length of the transmitting dipole, the length of the receive dipole, and the angle of orientation between the transmit dipole and receive dipole. The angle of orientation can be altered due to varying locations and orientations of IMD 80 or the different geometries of individual patients. Thus, no one single transmit or receive dipole will be optimal for all implant scenarios, particularly for enabling placement of external device 16 in an ergonomical manner.

Selecting among the plurality of electrodes 18e-h enables IMD 80 to adjust the angle of orientation between the dipole of IMD 80 and the dipole of external device 16. Even a slight adjustment of the angle of orientation, e.g., by switching from a dipole formed by electrodes 18a to 18e to a dipole formed by electrodes 18a and 18g may improve the quality and reliability of communication with external device 16. Moreover, such ability to adjust the angle of orientation between the dipole of IMD 80 and the dipole of external device 16 may allow for use of more ergonomical external devices, e.g., body-worn devices.

IMD 80 may selectively couple one of the electrodes 18*e-h* to the communication module of IMD 80 to function as the transmit and receive dipole in conjunction with electrode 18*a*. In one example, external device 16 may assess the signal quality of a received signal and send a command to IMD 80 to reconfigure the switch to couple to a different one of electrodes 18*e-h* when the signal quality is not sufficient. In another example, IMD 80 may assess the signal quality of a received signal and reconfigure the switch based on the assessment. In this manner, IMD 80 may be selectively configured between different dipole arrangements formed by electrodes positioned at different positions to provide a desirable signal quality for communication with an implantable medical device. The signal quality may be assessed using a variety of methods including but not limited to a transmission power required for signal detection, a received signal strength, a received signal-to-noise ratio, a bit error rate, a data throughput rate, a data dropout rate, a background noise floor, an optimum frequency, a correlation between a detected signal and a known template for a signal, or any combination of these measures.

It may be desirable to have a surface area of the electrodes used for intra-body communication be about the same size or a ratio of the larger electrode. In some examples, IMD 80 may connect the communication module to more than two electrodes. For example, IMD 80 may connect the communication module to electrode 18*a* and two of electrodes 18*e-h* concurrently (for a total of three electrodes) to change the effective electrode surface area and thus the impedance. In other words, by electrically connecting to three electrodes, the total surface area of the exposed fixation mechanism is increased thereby affecting the impedance. In this manner, IMD 80 may selectively adjust the impedance by selecting more or fewer electrodes. This may be particularly advantageous if the surface area of one of the electrodes for communication changes, e.g., due damage to the dielectric material somewhere along the fixation mechanism causing additional surface area to be exposed or tissue overgrowth that covers a portion of the exposed fixation mechanism decreasing the surface area of conductive fixation mechanism exposed.

In the example illustrated in FIG. 8, the length of the exposed portion of struts 82*a-d* forming electrodes 18*e-h*, respectively, are approximately the same. However, in other instances, the length of the exposed portion of each of struts 82*a-d* forming electrodes 18*e-h* (or a portion thereof) may be of different lengths. IMD 80 may selectively couple one of the electrodes 18*e-h* (formed by the exposed portion of struts 82*a-d*, respectively) to the communication module of IMD 80 to achieve a desired impedance or dipole length. In this manner, IMD 80 may selectively change the effective electrode surface area and thus the impedance. IMD 80 may, for example, make such an adjustment automatically upon initiating communication, make the adjustment in response to a signal quality below a certain level, or make the adjustment in response to a command from an another device (external or implanted).

Although illustrated in FIGS. 8A-8C as including four struts 82*a-d* extending from the end of housing 22, IMD 80 may include more of fewer struts 82. In fact, in one example IMD 80 may include only a single strut 82 that extends from the end of housing 22 (e.g., strut 82*d*) to increase the length of the dipole. In such a case, however, the IMD 20 does not provide dipole diversity.

Figure 9:
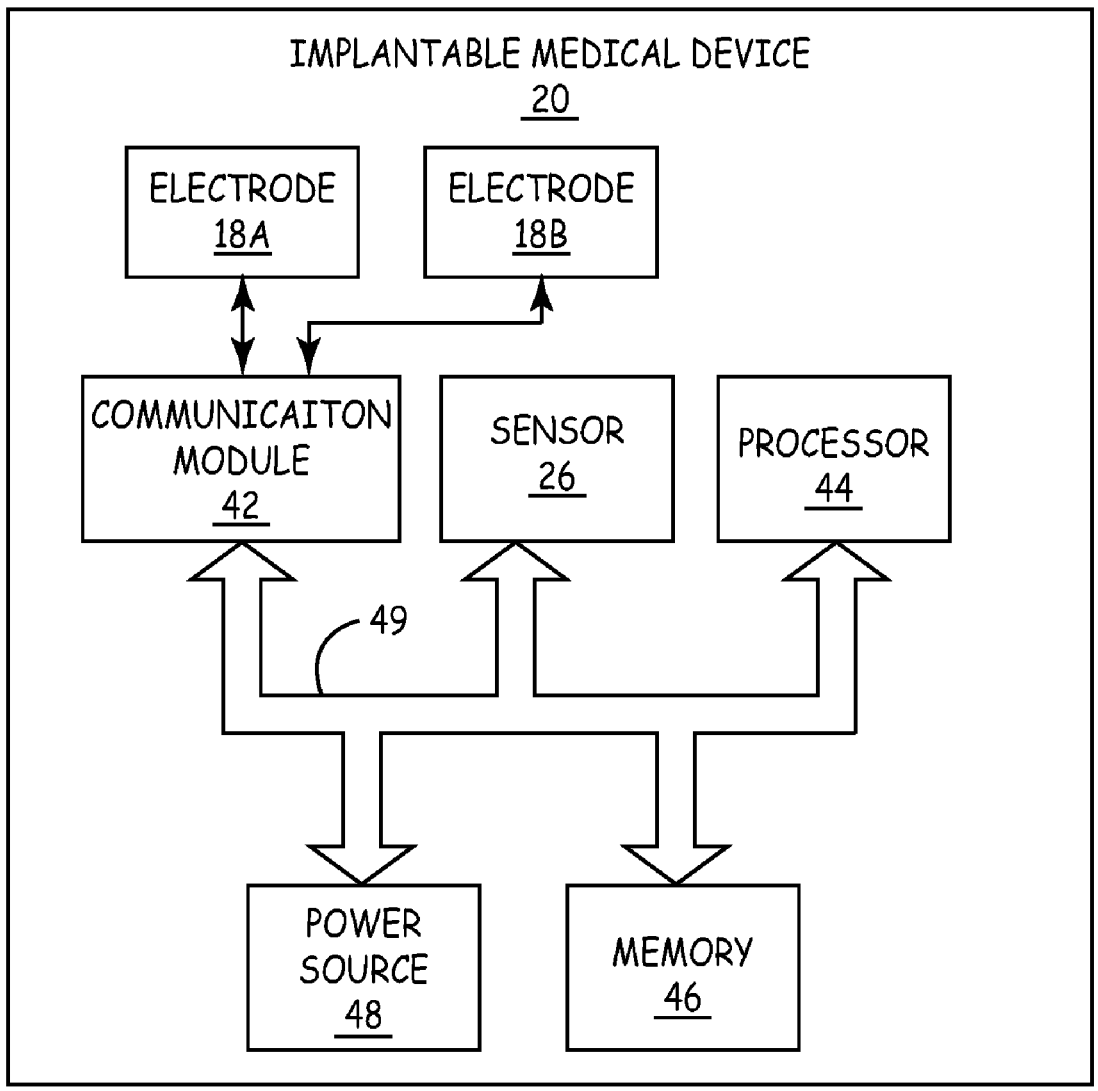
FIG. 9 is a functional block diagram illustrating components of an implantable medical device in further detail.

FIG. 9 is a functional block diagram illustrating components of an implantable medical device in further detail. FIG. 9 will be described with respect to IMD 20 for purposes of illustration. However, the implantable medical device may correspond to any of the other implantable medical devices described herein.

IMD 20 includes a pressure sensor 26, communication module 42, electrodes 18*a* and 18*b*, processor 44, memory 46 and power source 48. The components of IMD 20 are shown to be interconnected by a data/communication bus 49, but may be interconnected by other means including direct electrical or non-electrical connections or a combination of different types of connections.

As described above, IMD 20 may sense one or more parameters (e.g., physiological or biological parameters) of patient 12 and/or detect one or more conditions from the sensed parameters. For example, pressure sensor 26 may be configured to obtain signals related to the pressure of the surrounding environment within which IMD 20 is implanted. Although described with respect to IMD 20 including pressure sensor 26, IMD 20 may include any number and type of sensors depending on the type of device, including a pH sensor, oxygen sensor, temperature sensor, electrodes, or any other type of sensor.

The parameters sensed by pressure sensor 26 may be stored in memory 46. In some instances, the sensed parameters may be stored in raw form. In other instances, the sensed parameters may be processed and the processed parameters may be stored in memory 46. For example, IMD 20 may include one or more analog or digital components that amplify and filter the sensed parameters and store the filtered parameters in memory 46. The parameters stored in memory 46 may, in some cases, be retrieved and further processed by processor 44. Processor 44 may, for example, process the sensed parameters to monitor or detect a condition of patient 12.

Processor 44 may control operation of IMD 20 with the aid of instructions associated with program information stored in memory 46. For example, the instructions may define the timing at which to sample signal from pressure sensor 26 or, in instances in which implantable medical device 20 delivery therapy, the timing of therapy delivery, waveform characteristics for electrical stimulation, and/or dosing programs that specify an amount of a therapeutic agent to be delivered to a target tissue site within patient 12. Processor 44 may also control operation of communication module 42 to transmit communications to and/or receive communications from another medical device, such as external device 16 (FIG. 1) or another implanted medical device.

Communication module 42 is coupled to at least two electrodes 18*a* and 18*b* configured to function as an electric dipole and transmit and receive information encoded in electrical signals to and from external device 16. The electrical signals are typically transmitted and received in a modulated format such as frequency shift keying, amplitude shift keying, phase shift keying, pulse width modulation, pulse amplitude modulation, quadrature amplitude modulation, orthogonal frequency division multiplexing, spread spectrum techniques, or in an analog signal format and/or modulation technique such as analog amplitude modulation or frequency modulation. In some embodiments, the communication module 42 of IMD 14 can be configured to operate for periods of time in a sleep state in order to conserve battery power. In such a configuration, communication module 42 may be configured to wake up periodically to listen to a communication request from external device 16 or to transmit the stored parameters sensed by pressure sensor 26.

Communication module 42 may include any suitable hardware, firmware, software or any combination thereof for communicating with another device for transmitting and receiving intra-body communications. For example, communication module 42 may include a current source, modulator, demodulator, encoder, decoder, amplifier, frequency converter, filter or any other component desired for communicating using intra-body communication techniques.

Power source 48 delivers operating power to various components of IMD 20. Power source 48 may include, for example, a small rechargeable or non-rechargeable battery and a power generation circuit to produce the operating power. In some examples, power requirements may be small enough to allow IMD 20 to utilize patient motion and implement a kinetic energy-scavenging device to trickle charge a rechargeable battery. In other examples, traditional batteries may be used for a limited period of time. As a further alternative, an external inductive power supply may transcutaneously power IMD 20 whenever measurements are needed or desired.

IMD 20 of FIG. 9 is provided for purposes of illustration. IMD 20 may include more or fewer components than those illustrated in FIG. 9. For example, IMD 20 may include more than two electrodes coupled to communication module 42. Such an embodiment is described with respect to FIGS. 8A-8C. In such an embodiment, communication module 42 may be selectively configured to couple to the two electrodes of the plurality of electrodes that provide an adequate orientation with respect to the dipole of external device 16. To this end, communication module 42 may be coupled to the electrodes via a switching device (not shown) that may be configured to couple to the selected electrodes. Processor 44 may, for example, control the configuration of the switching device in response to a command from external device 16. In another example, communication module 42 or processor 44 may be configured to operate as a signal quality monitor and assess the signal quality of an electrical signal received from external device 16. In this case, communication module 42 or processor 44 may control the configuration of the switching device in response to the signal quality assessment to achieve dipole diversity.

As another example, IMD 20 may be an implantable medical device configured to also provide therapy, such as electrical stimulation therapy or drug delivery therapy, in accordance with parameters of one or more selected therapy programs. In this case, implantable sensor may include a therapy module (not shown) to generate therapy according to one or more therapy programs. In the case of electrical stimulation therapy, the therapy module may include a stimulation generator that generates and delivers electrical stimulation therapy, e.g., in the form of pulses or shocks. Processor 44 may control the stimulation generator to deliver electrical stimulation pulses with amplitudes, pulse widths, frequency, and/or electrode polarities specified by the one or more therapy programs. In the case of drug delivery therapy, the therapy module may include a pump that delivers a drug or therapeutic agent, e.g., via a catheter or other delivery mechanism. Processor 44 may control the pump to deliver the drug or therapeutic agent with the dosage and frequency (or rate) specified by the one or more therapy programs. As such, the techniques of this disclosure should not be considered limited to the example described in FIG. 9.

The techniques described in this disclosure may be implemented, at least in part, in hardware, software, firmware or any combination thereof. For example, various aspects of the techniques or components may be implemented within one or more processors, including one or more microprocessors, digital signal processors (DSPs), application specific integrated circuits (ASICs), field programmable gate arrays (FPGAs), programmable logic circuitry, or the like, either alone or in any suitable combination. The term "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read only memory (ROM), non-volatile RAM (NVRAM), electrically erasable programmable ROM (EEPROM), Flash memory, and the like. The instructions may be executed by a processor to support one or more aspects of the functionality described in this disclosure.

Various examples have been described. These examples, however, should not be considered limiting of the techniques described in this disclosure. These and other examples are within the scope of the following claims.

The invention claimed is:

1. An implantable medical device comprising:
a housing that encloses at least a communication module;
a first electrode electrically coupled to the communication module; and
an electrically conductive fixation mechanism that is mechanically coupled to the housing and electrically coupled to the communication module within the housing,
wherein the electrically conductive fixation mechanism includes a dielectric material that covers part of a surface of the fixation mechanism,
wherein a portion of the electrically conductive fixation mechanism is not covered by the dielectric material such that the portion of the electrically conductive fixation mechanism is exposed to form a second electrode that is electrically coupled to the communication module,
wherein the communication module is configured to communicate using the first electrode and second electrode.

2. The implantable medical device of claim 1, wherein the first electrode is located on the housing.

3. The implantable medical device of claim 2, wherein a portion of the housing forms the first electrode.

4. The implantable medical device of claim 2, wherein the portion of the electrically conductive fixation mechanism exposed to form the second electrode is located at a position on the fixation mechanism that is a further distance from the first electrode than any other portion of the housing.

5. The implantable medical device of claim 4, wherein the portion of the electrically conductive fixation mechanism exposed to form the second electrode is located at a position on the fixation mechanism that is a furthest distance from the first electrode.

6. The implantable medical device of claim 1,
further comprising a second electrically conductive mechanism that is mechanically coupled to the housing and electrically coupled to the communication module within the housing,
wherein the second electrically conductive mechanism includes a dielectric material that covers part of a surface of the fixation mechanism,
wherein a portion of the second electrically conductive mechanism is not covered by the dielectric material such that the portion of the second electrically conductive mechanism is exposed to form the first electrode.

7. The implantable medical device of claim 6, wherein the portion of the second electrically conductive mechanism exposed to form the first electrode is located at a position on the second conductive mechanism that is a further distance from the second electrode than any portion of the housing.

8. The implantable medical device of claim 6, further comprising:
at least a third electrically conductive mechanism that is mechanically coupled to the housing and electrically coupled to the communication module within the housing,
wherein the third electrically conductive mechanism includes a dielectric material that covers part of a surface of the third conductive mechanism,
wherein a portion of the third electrically conductive mechanism is not covered by the dielectric material such that the portion of the third electrically conductive mechanism is exposed to form a third electrode
a switching device electrically coupled between the communication module and the second and third conductive mechanisms, wherein the switching device selectively couples one of the second and third conductive mechanisms to the communication module.

9. The implantable medical device of claim 8, wherein the switching device selectively couples one of the second and third conductive mechanisms to the communication module based on a signal quality of a signal received by the implantable medical device.

10. The implantable medical device of claim 8, wherein the switching device selectively couples one of the second and third conductive mechanisms to the communication module in response to a command from an external device.

11. The implantable medical device of claim 8, wherein the switching device couples both of the second and third conductive mechanisms to the communication module concurrently.

12. The implantable medical device of claim 8, wherein
a surface area of the portion of the second electrically conductive mechanism exposed to form the second electrode is different than a surface area of the portion of the third electrically conductive mechanism exposed to form the third electrode; and
the switching device electrically couples one of the second electrode and the third electrode to the communication module based on least in part on the surface areas.

13. The implantable medical device of claim 12, wherein the portion of the electrically conductive fixation mechanism is not covered by the dielectric material is between approximately 10 and 20 percent of the electrically conductive fixation mechanism.

14. The implantable medical device of claim 6, wherein the electrically conductive fixation mechanism is mechanically coupled to a first end of the housing and the second conductive mechanism is mechanically coupled to a second end of the housing opposite the first end of the housing.

15. The implantable medical device of claim 1, wherein the portion of the electrically conductive fixation mechanism is not covered by the dielectric material is between approximately 5 and 30 percent of the electrically conductive fixation mechanism.

16. The implantable medical device of claim 1, wherein the fixation mechanism is a cylindrical stent-like structure that is configured to lodge against a vessel wall.

17. The implantable medical device of claim 1, wherein the fixation mechanism includes at least two fixation loops mechanically coupled to the housing.

18. The implantable medical device of claim 1, further comprising a sensor within the housing to sense at least one parameter of a patient.

19. An apparatus comprising:
a housing that includes:
a communication module; and
a sensor to sense at least one parameter of a patient;
a first electrode electrically coupled to the communication module; and
means for affixing the apparatus to a target location within a patient,
wherein the means for affixing is mechanically coupled to the housing and electrically coupled to the communication module within the housing,
wherein the means for affixing is formed of a conductive material partially covered by a dielectric material such that a portion of the conductive material is not covered by the dielectric material to form a second electrode that is electrically coupled to the communication module,
wherein the communication module is configured to communicate using intra-body communication via the first electrode and second electrode.

20. The apparatus of claim 19, wherein the portion of the conductive material not covered by the dielectric material is located at a position on the means for affixing that is a further distance from the first electrode than any portion of the housing.

21. The apparatus of claim 19, wherein the portion of the electrically conductive fixation mechanism that is not covered by the dielectric material is between approximately 5 and 30 percent of the means for affixing.

* * * * *